United States Patent [19]
Liu

[11] Patent Number: 5,961,493
[45] Date of Patent: Oct. 5, 1999

[54] AUTOMATIC SAFETY INFUSION CATHETER NEEDLE

[76] Inventor: Wen-Neng Liu, 19508 Nicholas Ave., Cerritos La., Calif. 90701

[21] Appl. No.: 09/238,023

[22] Filed: Jan. 26, 1999

Related U.S. Application Data

[63] Continuation-in-part of application No. 09/089,260, Jun. 3, 1998, Pat. No. 5,885,252.

[51] Int. Cl.$^6$ .................................................. A61M 5/178
[52] U.S. Cl. ........................................... 604/164; 604/167
[58] Field of Search .................................... 604/164, 264, 604/263, 165–168, 177, 174, 170

[56] References Cited

U.S. PATENT DOCUMENTS

| | | | |
|---|---|---|---|
| 5,542,930 | 8/1996 | Schur | 604/164 |
| 5,885,251 | 3/1999 | Luther | 604/164 X |
| 5,902,274 | 5/1999 | Yamamoto et al. | 604/164 |

*Primary Examiner*—John D. Yasko
*Attorney, Agent, or Firm*—Rosenberg, Klein & Bilker

[57] ABSTRACT

An automatic safety infusion catheter needle including: a trifurcate connector having a first and a second connecting sections coaxially aligned with each other and a third connecting section serially connected with an infusion catheter; an infusion soft needle inserted on the first connecting section of the trifurcate connector; and a steel needle device including a steel needle body and a protective sleeve. A base seat of a bottom end of the steel needle body is normally resiliently and slidably latched in the protective sleeve. A top section of the protective sleeve is snugly fitted with the second connecting section of the trifurcate connector. A needle holder upward projects from the base seat of the steel needle body. A steel needle is coaxially inserted with the needle holer. The steel needle is passed through the top end of the protective sleeve and coaxially fitted in the soft needle. The needle holder is formed with guide hole for guiding a liquid medicine to smoothly flow out. In use, the soft needle together with the steel needle is thrusted into the vein of a patient and then the steel needle body is unlatched from the protective sleeve. At this time, a spring automatically resiliently restores and the steel needle body is bounded and dropped into the protective sleeve and hidden therein so as to facilitate processing of medical waste.

6 Claims, 10 Drawing Sheets

AUTOMATIC SAFETY INFUSION CATHETER NEEDLE

CROSS-REFERENCE TO RELATED APPLICATION

This application is a Continuation-in-Part of U.S. patent application Ser. No. 09/089,260, entitled "An Automatic Safety Infusion Catheter Needle", filed on Jun. 3, 1998, now U.S. Pat. No. 5,885,252.

BACKGROUND OF THE INVENTION

Figure 1:
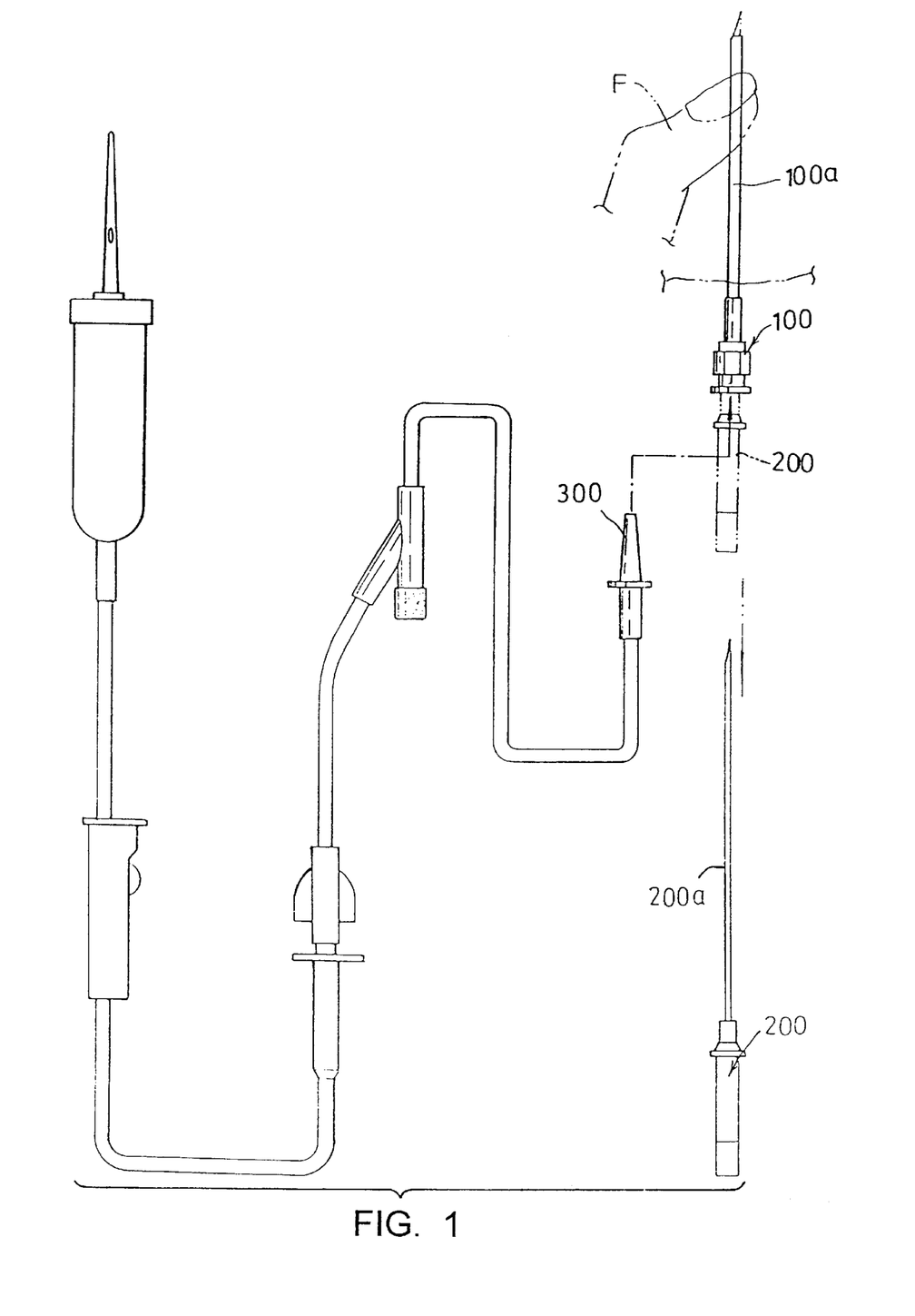
FIG. 1 shows a conventional intravenous catheter needle.
Figure 2:
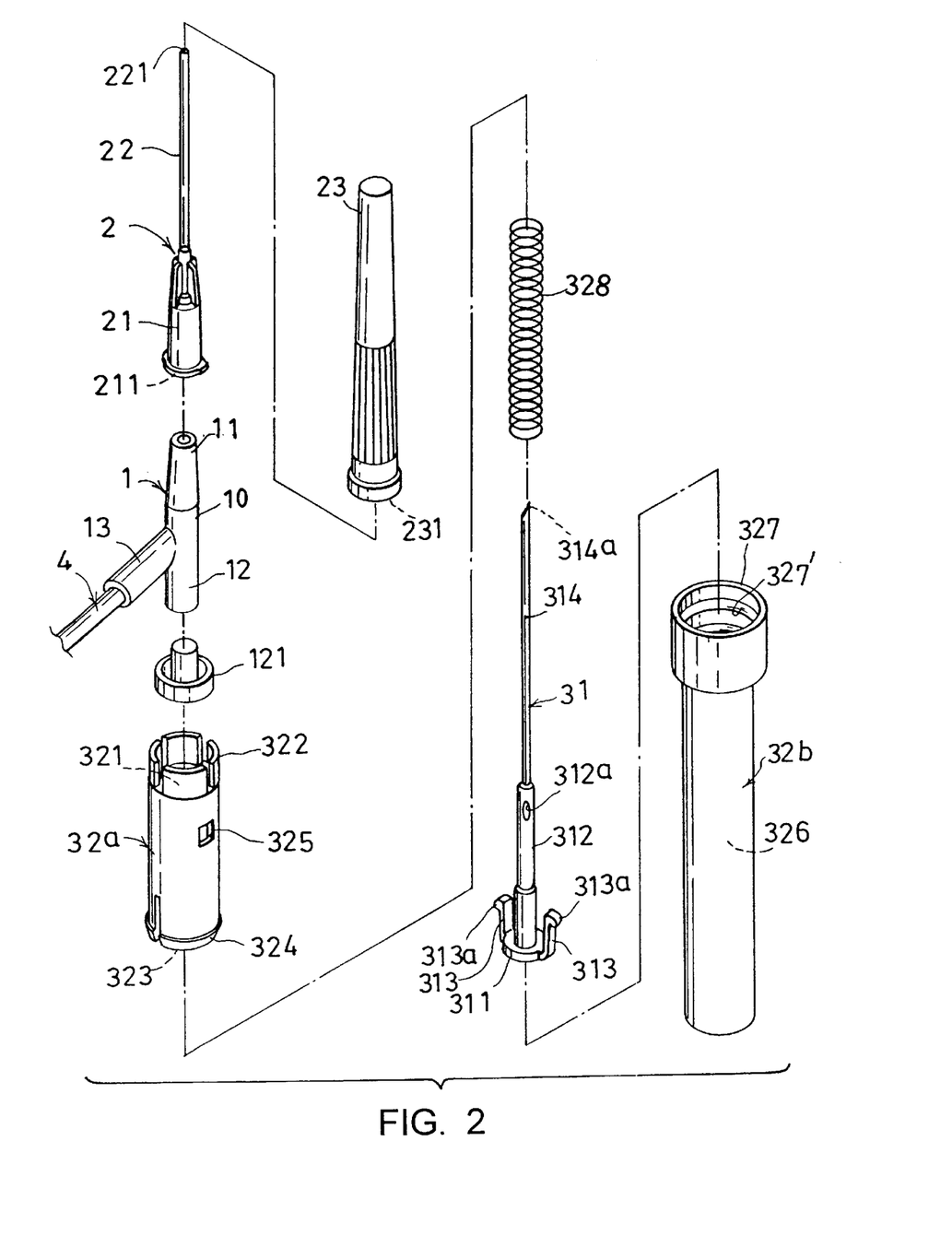
FIG. 2 is a perspective exploded view of the present invention.

The existing infusion catheter needle employs one single injection needle for intravenous injection. As shown in FIG. 1, such catheter needle includes an infusion soft needle 100 and a steel needle 200. The needle body 200a of the steel needle 200 is passed through the needle body 100a of the soft needle 100 for hardening the soft needle body 100a, whereby the soft needle body 100a can be smoothly thrusted into the vein of a patient. After the soft needle body 100a is thrusted into the vein, the medical personnel must press the soft needle body 100a with one hand F to avoid back flow of the blood of the patient and draw the steel needle 200 backward from the soft needle 100 with the other hand. Then an infusion catheter 300 is serially connected with the soft needle 100 to complete the injection procedure. In use, the above catheter needle has some shortcomings as follows:

1. When pressing the soft needle body 100a with one hand, the medical personnel must draw the steel needle 200 from the soft needle 100 with the other hand. Moreover, the medical personnel must then connect the infusion catheter 300 with the soft needle 100. It is quite inconvenient to perform all these procedures at the same time.

2. After the steel needle 200 is drawn from the soft needle 100, the steel needle 200 is exposed outside and tends to impale the medical personnel. Therefore, the medical personnel may be infected with AIDS, hepatitis, etc. This is extremely dangerous to the medical personnel.

SUMMARY OF THE INVENTION

It is therefore a primary object of the present invention to provide an automatic safety infusion catheter needle including: a trifurcate connector having a first and a second connecting sections coaxially aligned with each other and a third connecting section serially connected with an infusion catheter; an infusion soft needle inserted on the first connecting section of the trifurcate connector; and a steel needle device including a steel needle body and a protective sleeve. A base seat of a bottom end of the steel needle body is normally resiliently and slidably latched in the protective sleeve. A top section of the protective sleeve is snugly fitted with the second connecting section of the trifurcate connector. A needle holder upward projects from the base seat of the steel needle body. A steel needle is coaxially inserted with the needle holer. The steel needle is passed through the top end of the protective sleeve and coaxially fitted in the soft needle. The needle holder is formed with guide hole for guiding a liquid medicine to smoothly flow out. In use, the soft needle together with the steel needle is thrusted into the vein of a patient and then the steel needle body is unlatched from the protective sleeve. At this time, a spring automatically resiliently restores and the steel needle body is bounded and dropped into the protective sleeve and hidden therein so as to facilitate processing of medical waste.

The present invention can be best understood through the following description and accompanying drawings, wherein:

DETAILED DESCRIPTION OF THE PREFERRED EMBODIMENTS

Please refer to FIGS. 2 to 6. The present invention includes: a trifurcate connector 1 having a first and a second connecting sections 11, 12 coaxially aligned with each other, a third connecting section 13 of the trifurcate connector 1 being serially connected with an infusion catheter 4; an infusion soft needle inserted on the first connecting section 11 of the trifurcate connector 1; a steel needle device 3 including a steel needle body 31 and a protective sleeve 32, a bottom end of the steel needle body 31 being normally resiliently and slidably latched in the protective sleeve 32, a top section of the protective sleeve 32 being snugly fitted with the second connecting section 12 of the trifurcate connector 1, a steel needle 314 inserted with the steel needle body 31 being coaxially passed through the soft needle. Accordingly, in injection, the soft needle 2 together with the steel needle 314 is thrusted into the vein of the patient. Then the steel needle body 31 is unlatched from the protective sleeve 32 and automatically bounded and dropped into the protective sleeve 32 and hidden therein so as to facilitate processing of medical waste.

The trifurcate connector 1 is made of plastic material, including a main body 10. An upper section of the main body 10 is defined as the first connecting section 11. A lower section of the main body 10 is defined as the second connecting section 12. The end of the second connecting section 12 is fitted with the rubber cap 121. The first and second connecting sections 11, 12 are coaxially aligned with each other about the central axis 10a of the main body 10. The third connecting section 13 outward projects from a middle section of the main body for connecting with the infusion catheter 4.

The infusion soft needle 2 includes: a needle holder 21 formed with a fitting socket 211 at bottom end for fitting with the first connecting section 11 of the trifurcate connector; a soft needle body 22 upward extending from the top end of the needle holder 21 and formed with an axial injection passage 221; and a needle sheath 23 formed with a protective cavity 231 for fitting around the needle holder 21 to enclose the soft needle body 22.

Figure 5:
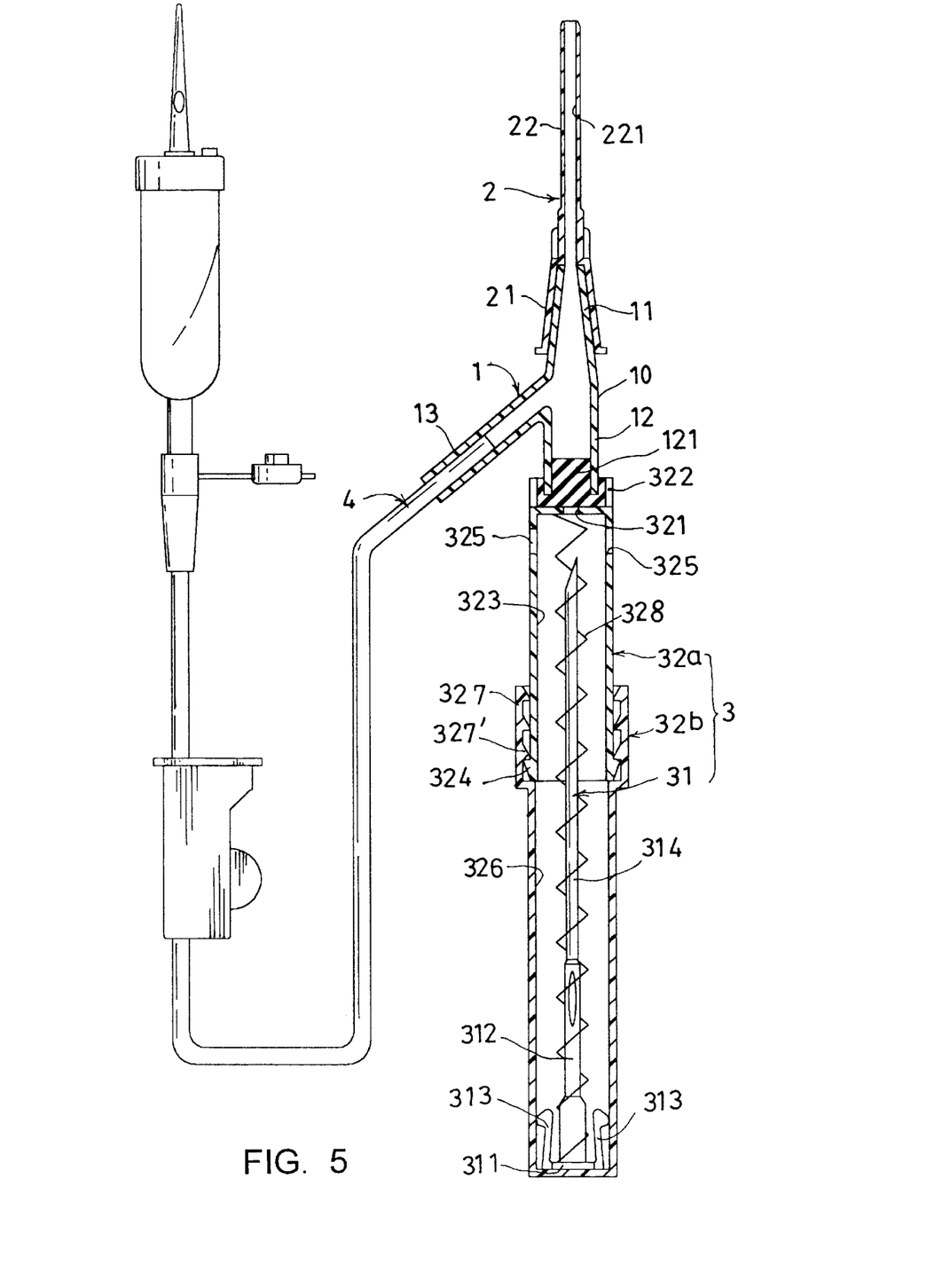
FIG. 5 is a sectional view showing that the steel needle body is totally bounded and dropped into the protective sleeve.
Figure 6:
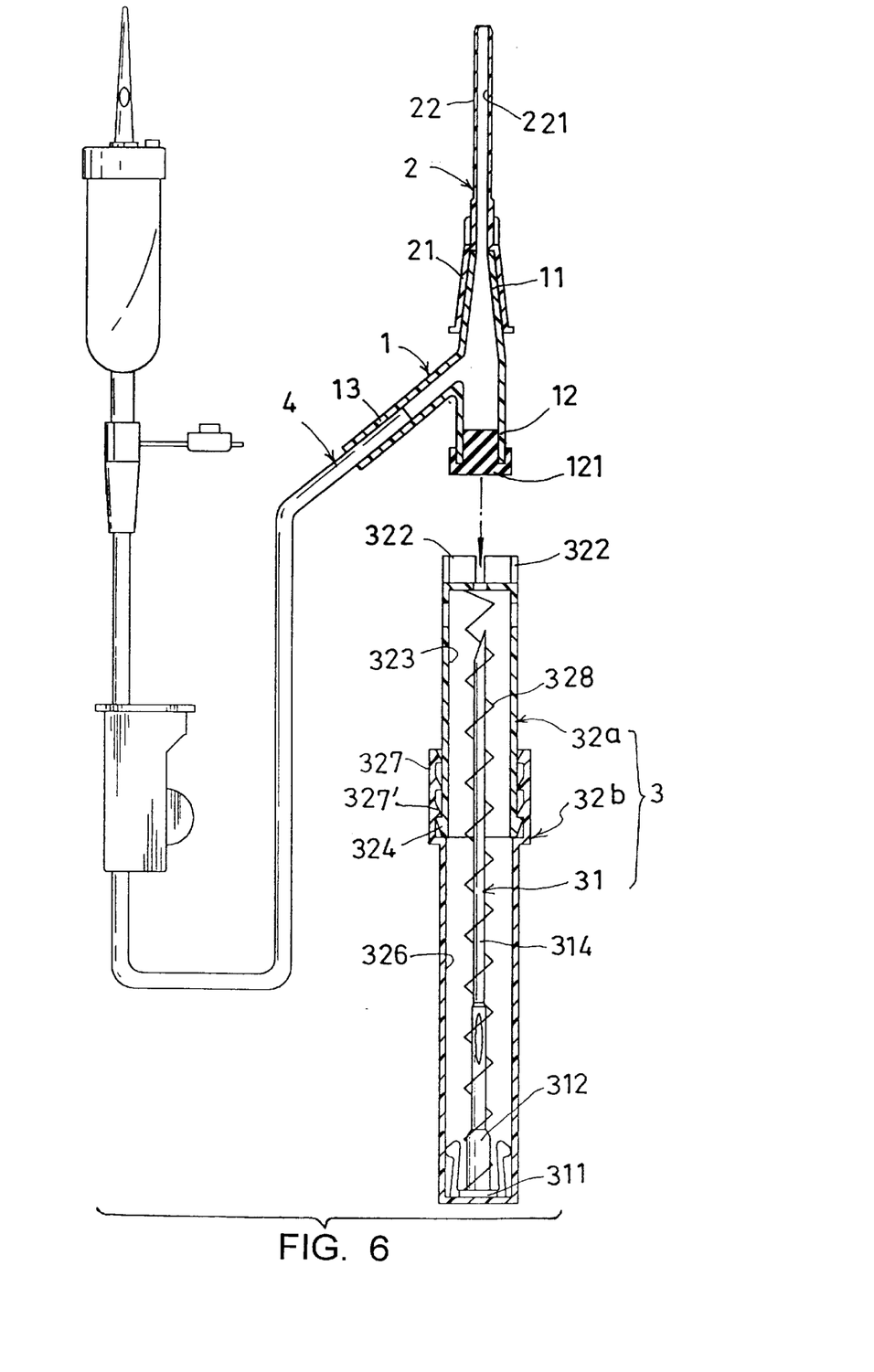
FIG. 6 is a view according to FIG. 5, showing that the steel needle device is disconnected from the trifurcate connector.
Figure 7:
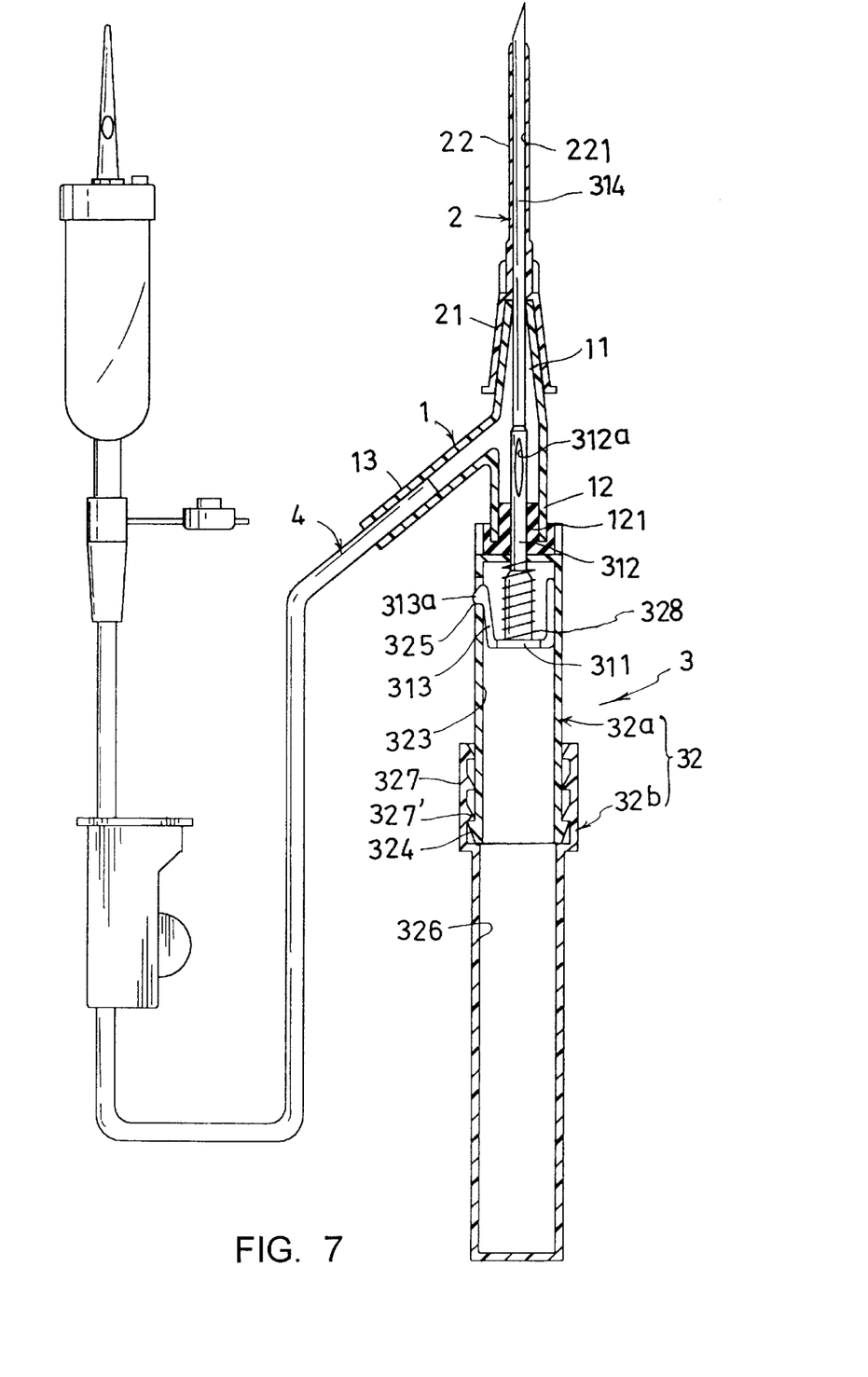
FIG. 7 is a sectional view of a second embodiment of the present invention.

Referring to FIGS. 2 to 6, the steel needle device 3 includes: a steel needle body 31 the bottom end of which is formed with a base seat 311, a needle holder 312 axially upward extending from the base seat 311, the needle holder 312 being formed with at least one radial guide hole 312a, at least one latch arm 313 (FIGS. 2 to 6 show multiple latch arms 313, while FIG. 7 shows only one single latch arm 313) extending from an outer edge of bottom end of the base seat 311, a free end of the latch arm 313 being disposed with a projecting latch hook section 313a for correspondingly resiliently latching in a latch hole 325 of the protective sleeve 32, a hollow steel needle 314 being fitted into a top end of the needle holder 312 with the central through hole 314a of the steel needle 314 communicating with the guide hole 312a; and a protective sleeve 32 composed of an upper and a lower sleeves 32a, 32b fitted with each other. A top end of the upper sleeve 32a is formed with a central axial through hole 321, permitting the steel needle 314 and an upper section of the needle holder 312 to pass therethrough. A cylindrical clamping section 322 upward extends from the top end of the upper sleeve 32a for firmly embracing the rubber cap 121 inserted with the second connecting section 12 of the trifurcate connector. A bottom end of the upper sleeve 32a is formed with an upward extending upper cavity 323 for slidably receiving therein the base seat 311 of the steel needle body 31. At least one hook section 324 outward projects from an outer edge of bottom end of the upper sleeve 32a for latching with the lower sleeve 32b. The wall of the upper sleeve 32a is formed with at least one latch hole 325 for latching with the latch hook section 313a of the latch arm of the steel needle body 31. The top end of the lower sleeve 32b is formed with a central axial lower cavity 326 which downward extends for slidably receiving therein the steel needle body 31. The top section of the lower sleeve 32b is formed with a latch tube section 327. The inner wall of the latch tube section 327 is disposed with at least one projecting latch tooth 327' for latching with the hook section 324 of the upper sleeve 32a so as to firmly connect the lower sleeve 32b under the upper sleeve 32a. The steel needle device 3 further includes a spring 328 normally compressed between the upper cavity 323 and the base seat 311 of the steel needle body. The spring 328 normally downward resiliently pushes the steel needle body 31. When the steel needle body 31 is unlatched from the protective sleeve 32, the spring 328 resiliently restores and extends to downward push the steel needle body 31 into the protective sleeve 32.

The cylindrical clamping section 322 of the upper sleeve 32a is composed of multiple resilient clamping jaws which are annularly arranged on the top end face of the upper sleeve 32a and axially upward project therefrom. The clamping jaws serve to firmly embrace the rubber cap 121 fitted with the second connecting section 12 of the trifurcate.

The needle holder 312 of the steel needle body 31 is passed through the rubber cap 121 of the second connecting section 12 with the steel needle 314 slidably positioned in the soft needle body 22. At this time, the guide hole 312a of the needle holder 312 is positioned above the rubber cap 121 for communicating with the infusion catheter 4 connected with the third connecting section 13 of the trifurcate connector 1. Accordingly, the liquid medicine can flow out from the guide hole 312a along the central through hole 314a of the steel needle 314.

Figure 3:
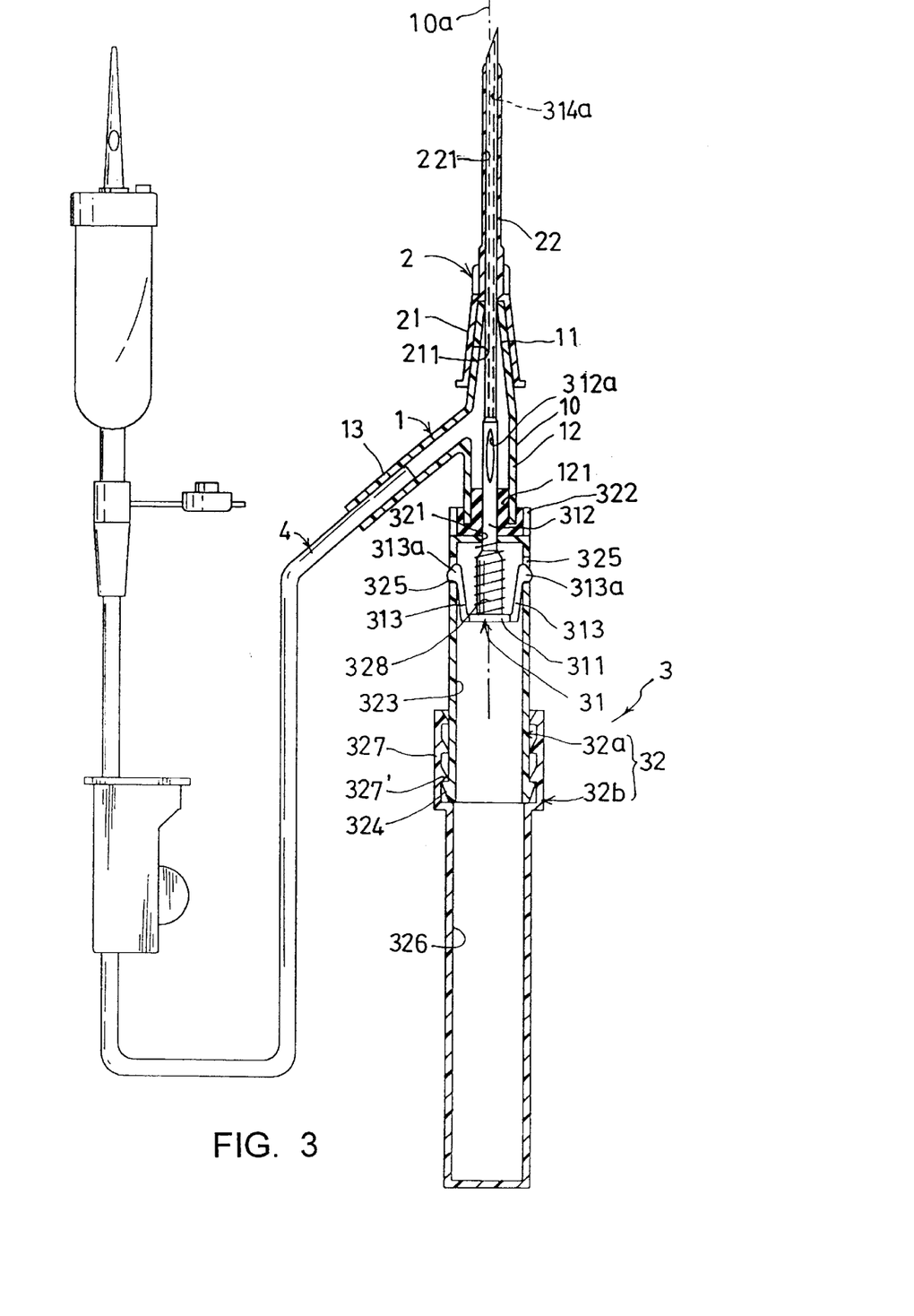
FIG. 3 is a sectional assembled view of the present invention in use.
Figure 4:
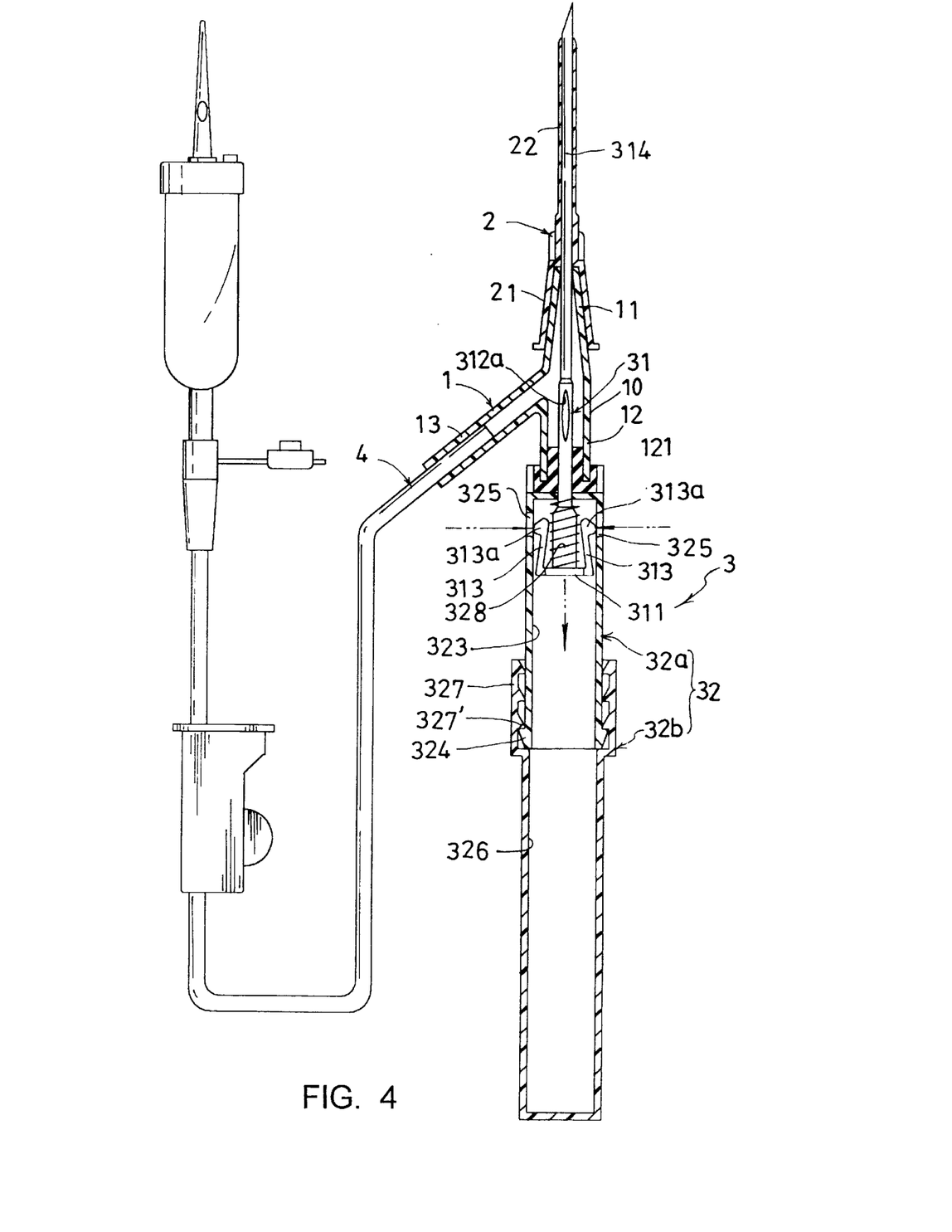
FIG. 4 is a sectional view according to FIG. 3, showing that the steel needle body is just unlatched from the protective sleeve.

In use, the infusion catheter 4 is first connected with the third connecting section 13 of the trifurcate connector 1. Then the needle sheath 23 is removed from the soft needle 2. At this time, as shown in FIG. 3, the air contained in the infusion catheter 4 is exhausted outside through the guide hole 312a of the steel needle body 31 and the central through hole 314a of the steel needle 314. Therefore, the liquid medicine contained in the infusion catheter 4 (such as a dropper) can smoothly flow out. This makes the infusion catheter 4 and the trifurcate connector 1 full of the liquid medicine so as to prevent the air in the infusion catheter 4 from being injected into human body to cause accident. At this time, the steel needle 314 of the steel needle body 31 is slidably fitted in the soft needle body 22 of the soft needle 2, providing a sufficient strength therefor to smoothly thrust into the vein of a patient. The rubber cap 121 fitted with the end of the second connecting section 12 resiliently embraces the needle holder 312 of the steel needle body 31 so that the liquid medicine flowing from the infusion catheter 4 into the trifurcate connector 1 will not leak from the second connecting section 12. As shown in FIGS. 4 and 5, thereafter, the medical personnel can compress the latch arm 313 of the steel needle body 31 so as to unlatch the latch hook section 313a of the latch arm 313 from the latch hole 325 of othe protective sleeve 32. At this time, the spring 328 resiliently restores to automatically downward push the steel needle body 31 and make the steel needle body 31 drop into the upper and lower cavities 323, 326 of the protective sleeve 32. Thereafter, the medical personnel can pull back and extract the steel needle 314 out of the soft needle body 22. When the steel needle 314 is totally drawn out of the rubber cap 121, as shown in FIGS. 5 and 6, the rubber cap 121 automatically resiliently seals the perforation thrusted by the needle holder 312 and the steel needle 314 and again seals the opening of the second connecting section 12 of the trifurcate connector 1. Therefore, the steel needle body 31 is totally hidden in the protective sleeve 32. At this time, the medical personnel can directly take down the protective sleeve 32 with the steel needle 314 hidden therein and discard the same for processing. As shown in FIG. 6, after the steel needle 314 of the steel needle body 31 is totally extracted from the soft needle body 22, the liquid medicine flowing from the third connecting section 13 into the trifurcate connector 1 will automatically flow from the first connecting section 11 through the soft needle 2 into the body of the patient. In the case that it is necessary to inject other liquid medicine, an injection syringe can be thrusted into the rubber cap 121 at the end of the second connecting section 12 to perform the injection procedure.

The infusion catheter 4 can be a dropper infusion throttle tube for forming a set of dropper syringe. However, the pattern and type of the infusion catheter 4 of the present invention are not limited.

Figure 8:
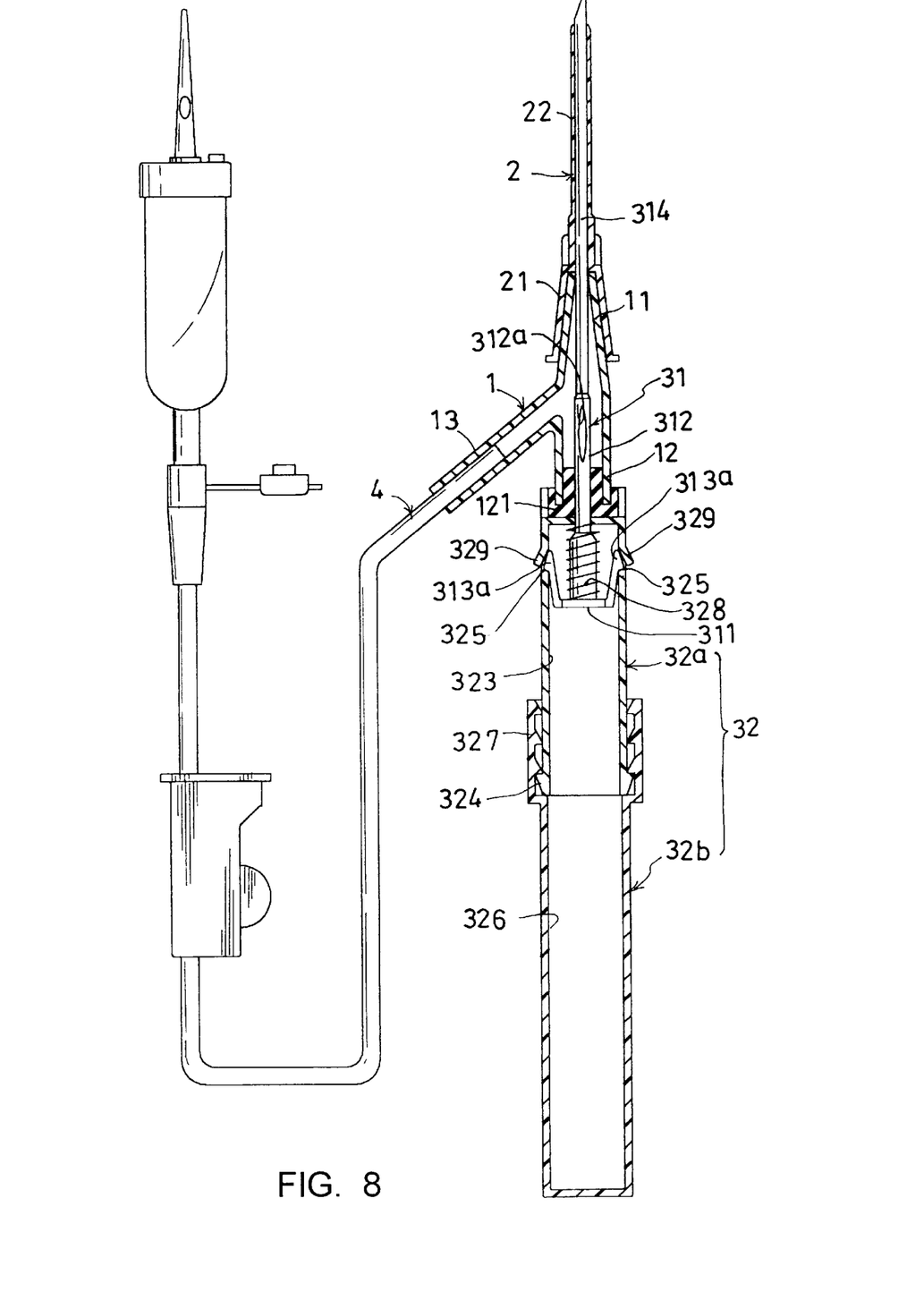
FIG. 8 is a sectional view of a third embodiment of the present invention.

Please refer to FIG. 8. The protective sleeve 32 can be modified to have a resilient pressing plate 329 which outward inclinedly extends from the edge of the latch hole 325 of the upper sleeve 32a. After a medical personnel presses the resilient pressing plate 329 from outer side, the latch hook section 313a of the latch arm of the steel needle body 31 is forcedly disengaged from the latch hole 325, whereby the steel needle body 31 is unlatched from the protective sleeve 32. At this time, the spring 328 can resiliently automatically bound the steel needle body 31 into the protective sleeve 32.

Figure 9:
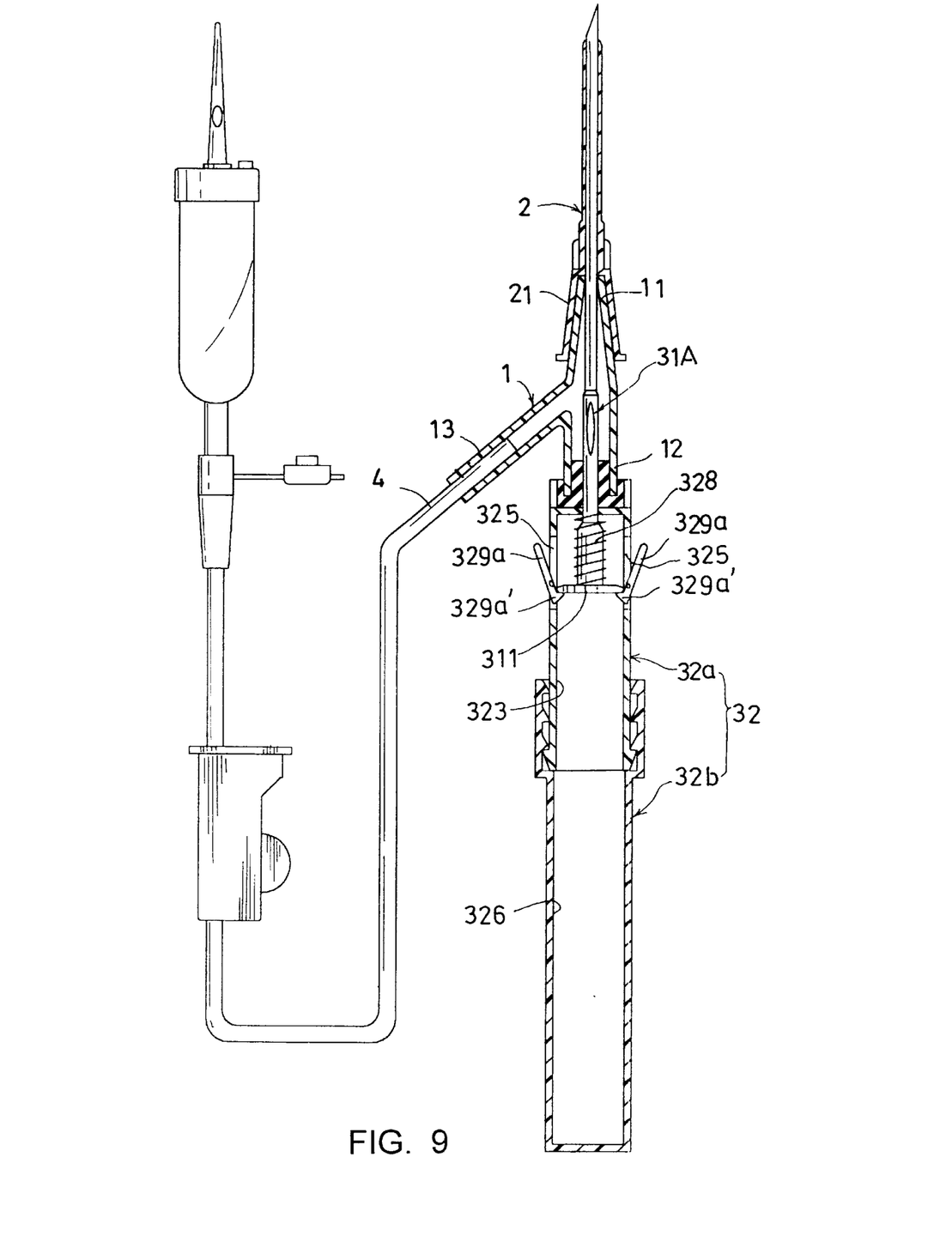
FIG. 9 is a sectional view of a fourth embodiment of the present invention.

FIG. 9 shows another modification of the protective sleeve 32 in which two prying plates 329a are inclinedly pivotally connected to two opposite edges of the latch holes 325 of the upper sleeve 32a. A bottom end of the prying plate 329a is formed with a hook section 329a' extending into the protective sleeve 32 for normally hooking and latching with the bottom edge of the base seat 311 of the steel needle body 31A. (In this embodiment, the latch arm of the steel needle body is omitted.) A top section of the prying plate 329a inclinedly projects out of the protective sleeve 32. After the top section of the prying plate 329a is pressed from the outer side, the hook section 329a' of the bottom end of the prying plate 329a is responsively deflected outward to unlatch from the bottom edge of the base seat 311 of the steel needle body 31A. At this time, the spring 328 compressed between the steel needle body 31A and the protective sleeve 32 resiliently restores to automatically bound the steel needle body 31A into the upper and lower cavities 323, 326 of the protective sleeve 32.

Figure 10:
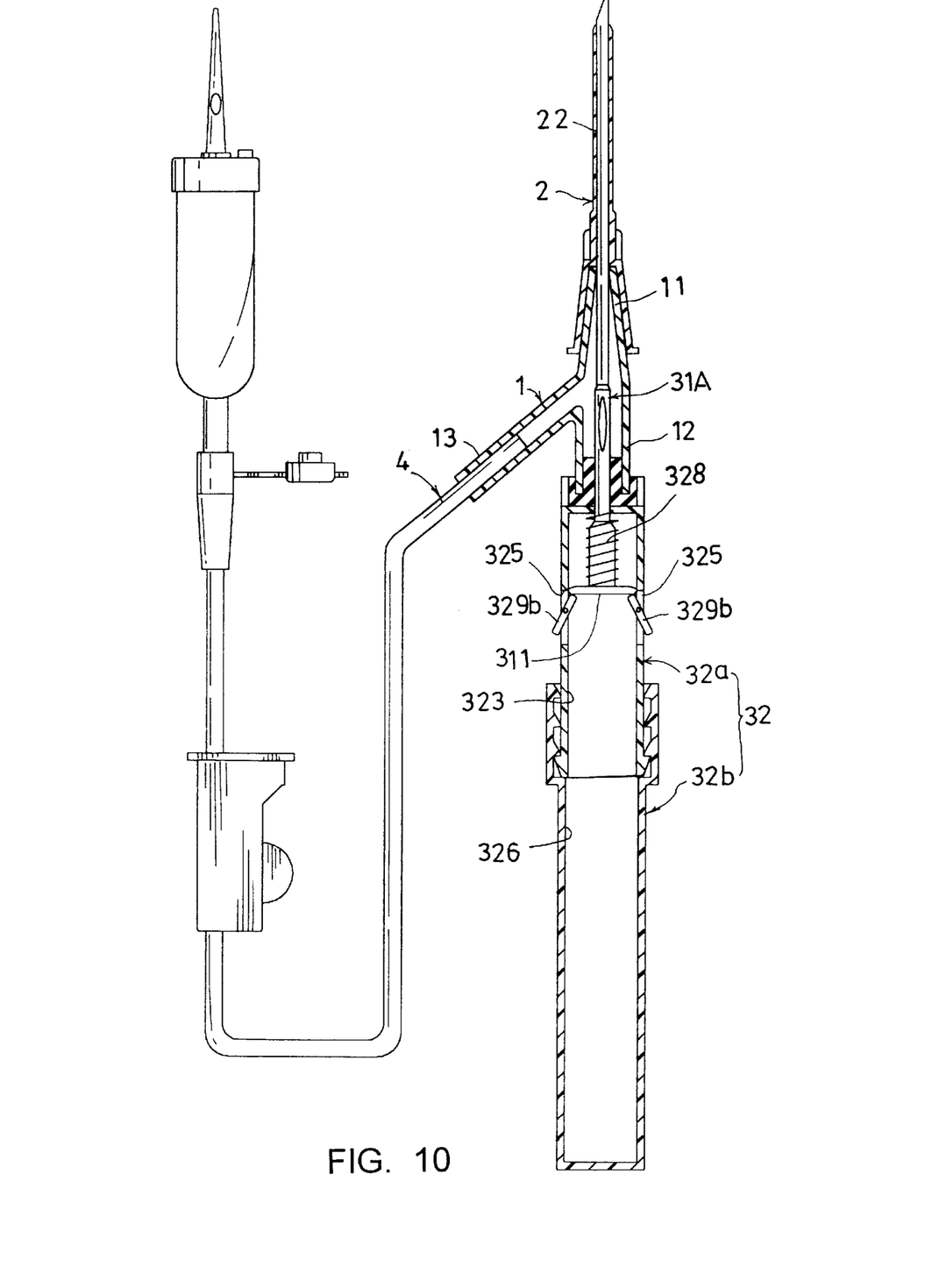
FIG. 10 is a sectional view of a fifth embodiment of the present invention.

FIG. 10 shows still another modification of the protective sleeve 32 in which two stopper plates 329b are inclinedly pivotally connected to two opposite edges of the latch holes 325 of the upper sleeve 32a. A top end of the stopper plate 329b extends into the protective sleeve 32 to normally abut against the bottom edge of the base seat 311 of the steel needle body 31A. (In this embodiment, the latch arm of the steel needle body is omitted.) A bottom section of the stopper plate 329b inclinedly projects out of the protective sleeve 32. After the bottom section of the stopper plate 329b is pressed from the outer side, the stopper plate 329b is responsively deflected outward to unlatch from the bottom edge of the base seat 311 of the steel needle body 31A. At this time, the spring 328 compressed between the steel needle body 31A and the protective sleeve 32 resiliently restores to automatically bound the steel needle body 31A into the upper and lower cavities 323, 326 of the protective sleeve 32.

According to the above arrangement, the bottom end of the steel needle body 31 of the steel needle device 3 normally resiliently and slidably fitted in and latched with the protective sleeve 32. In operation, a medical personnel only needs to unlatch the steel needle body 31 from the protective sleeve 32 so as to quickly automatically bound and drop the steel needle body 31 into the protective sleeve 32. Therefore, the steel needle body 31 is totally hidden in the protective sleeve 32 to facilitate the processing of medical waste.

It is to be understood that the above description and drawings are only used for illustrating some embodiments of the present invention, not intended to limit the scope thereof. Any variation and derivation from the above description and drawings should be included in the scope of the present invention.

What is claimed is:

1. An automatic safety infusion catheter needle comprising:
    a trifurcate connector having a hollow main body, an upper section of the main body being defined as a first hollow connecting section, a lower section of the main body being defined as a second hollow connecting section, the first and second connecting sections being coaxially aligned with each other about a central axis of the main body, a free end of the second connecting section being inserted with a rubber cap, a third connecting section outward projecting from a section between the first and second connecting sections of the main body for connecting with an infusion catheter;
    an infusion soft needle including a needle holder formed with a fitting socket at bottom end for fitting with the first connecting section of the trifurcate connector, a soft needle body connecting with and upward extending from a top end of the needle holder;
    a steel needle device including a steel needle body and a protective sleeve, a base seat of a bottom end of the steel needle body being normally resiliently and slidably latched in an upper section of the protective sleeve, a spring being resiliently compressed between the steel needle body and the protective sleeve for normally downward pushing the steel needle body, a top section of the protective sleeve being snugly fitted with the second connecting section of the trifurcate connector, a needle holder upward projecting from the base seat of the steel needle body, a steel needle being coaxially inserted with the needle holer, the steel needle being passed through the top end of the protective sleeve and coaxially fitted in the soft needle, the needle holder being formed with guide hole for guiding a liquid medicine to smoothly flow out, whereby when the steel needle body is unlatched from the protective sleeve, the spring compressed between the steel needle body and the protective sleeve resiliently restores so that the steel needle body is automatically bounded and dropped into the protective sleeve and hidden therein.

2. An automatic safety infusion catheter needle as claimed in claim 1, wherein the steel needle device includes: a steel needle body the bottom end of which is formed with a base seat, a needle holder axially upward extending from the base seat, the needle holder being formed with at least one radial guide hole, at least one latch arm extending from an outer edge of bottom end of the base seat, a free end of the latch arm being disposed with a projecting latch hook section, a hollow steel needle being fitted into a top end of the needle holder with the central through hole of the steel needle communicating with the guide hole; and a protective sleeve composed of an upper and a lower sleeves fitted with each other, a top end of the upper sleeve being formed with a central axial through hole, a cylindrical clamping section upward extending from the top end of the upper sleeve for firmly embracing the rubber cap inserted with the second connecting section of the trifurcate connector, a bottom end of the upper sleeve being formed with an upward extending upper cavity for slidably receiving therein the base seat of the steel needle body, at least one hook section outward projecting from an outer edge of bottom end of the upper sleeve, a wall of the upper sleeve being formed with at least one latch hole for latching with the latch hook section of the latch arm of the steel needle body, the top end of the lower sleeve being formed with a central axial lower cavity which downward extends for slidably receiving therein the steel needle body, the top section of the lower sleeve being formed with a latch tube section, the inner wall of the latch tube section being disposed with at least one projecting latch tooth for latching with the hook section of the upper sleeve, the steel needle device further including a spring normally compressed between the upper cavity and the base seat of the steel needle body.

3. An automatic safety infusion catheter needle as claimed in claim 2, wherein a resilient pressing plate outward inclinedly extends from an edge of the latch hole of the upper sleeve, whereby after the resilient pressing plate is pressed from outer side, the latch hook section of the latch arm of the steel needle body is forcedly disengaged from the latch hole.

4. An automatic safety infusion catheter needle as claimed in claim 1, wherein the protective sleeve is formed with at least one latch hole, at least one prying plate being inclinedly pivotally connected to opposite edges of the latch hole, a bottom end of the prying plate being formed with a hook section extending into the protective sleeve for normally hooking and latching with the bottom edge of the base seat of the steel needle body, a top section of the prying plate inclinedly projecting out of the protective sleeve, whereby after the top section of the prying plate is pressed from the outer side, the hook section of the bottom end of the prying plate is responsively deflected outward to unlatch from the bottom edge of the base seat of the steel needle body so that the spring compressed between the steel needle body and the protective sleeve resiliently restores to automatically bound the steel needle body into the upper and lower cavities of the protective sleeve.

5. An automatic safety infusion catheter needle as claimed in claim 1, wherein the protective sleeve is formed with at least one latch hole, at least one stopper plate being inclinedly pivotally connected to opposite edges of the latch holes, a top end of the stopper plate extending into the protective sleeve to normally abut against the bottom edge of the base seat of the steel needle body, a bottom section of the stopper plate inclinedly projecting out of the protective sleeve, whereby after the bottom section of the stopper plate is pressed from the outer side, the stopper plate is responsively deflected outward to unlatch from the bottom edge of the base seat of the steel needle body, so that the spring compressed between the steel needle body and the protective sleeve resiliently restores to automatically bound the steel needle body into the upper and lower cavities of the protective sleeve.

6. An automatic safety infusion catheter needle as claimed in claim 2, wherein the cylindrical clamping section of the upper sleeve is composed of multiple resilient clamping jaws which are annularly arranged on the top end face of the upper sleeve and axially upward project therefrom, the clamping jaws serving to firmly embrace the rubber cap fitted with the second connecting section of the trifurcate.

* * * * *